(12) United States Patent
Wang et al.

(10) Patent No.: US 8,512,533 B2
(45) Date of Patent: Aug. 20, 2013

(54) BIOSENSOR, BIOSENSOR PACKAGE STRUCTURE HAVING SAME, AND METHOD FOR FABRICATING SAME

(75) Inventors: Xue-Shen Wang, Beijing (CN); Qun-Qing Li, Beijing (CN); Shou-Shan Fan, Beijing (CN)

(73) Assignees: Tsinghua University, Beijing (CN); Hon Hai Precision Industry Co., Ltd., New Taipei (TW)

( * ) Notice: Subject to any disclaimer, the term of this patent is extended or adjusted under 35 U.S.C. 154(b) by 195 days.

(21) Appl. No.: 13/008,146

(22) Filed: Jan. 18, 2011

(65) Prior Publication Data
US 2012/0107178 A1    May 3, 2012

(30) Foreign Application Priority Data
Oct. 27, 2010    (CN) .......................... 2010 1 0521439

(51) Int. Cl.
*G01N 33/50*    (2006.01)
(52) U.S. Cl.
USPC .................. 204/403.01; 422/82.01; 422/68.1; 977/750; 977/752; 977/742; 977/746; 977/924; 435/6.1; 435/7.1; 435/287.1; 435/287.2; 204/403.15; 204/294

(58) Field of Classification Search
USPC ........................ 977/742–752, 924; 257/253; 204/400–403.15; 435/6.1, 6.19, 7.1, 287.1, 435/287.2; 422/82.01, 82.02, 68.1
See application file for complete search history.

(56) References Cited

U.S. PATENT DOCUMENTS

| 2006/0177946 A1* | 8/2006 | Dubin ............................... 438/1 |
| 2009/0215276 A1* | 8/2009 | Vereecken et al. ............ 438/758 |
| 2010/0079130 A1 | 4/2010 | Hong et al. |
| 2010/0133510 A1* | 6/2010 | Kim et al. ........................ 257/24 |
| 2011/0244585 A1* | 10/2011 | Mayne-L'Hermite et al. . 436/93 |

FOREIGN PATENT DOCUMENTS

| CN | 101126735 | | 2/2008 |
| CN | 101685077 | | 3/2010 |
| WO | WO 2010-034840 | * | 4/2010 |
| WO | WO 2010-059687 | * | 5/2010 |

* cited by examiner

*Primary Examiner* — J. Christopher Ball
*Assistant Examiner* — Jennifer Dieterle
(74) *Attorney, Agent, or Firm* — Altis Law Group, Inc.

(57) ABSTRACT

A biosensor includes a plurality of electrodes and a receptor. The plurality of electrodes comprises a plurality of carbon nanotubes. The receptor are located between the plurality of electrodes and electrically connected to the plurality of carbon nanotubes of the plurality of electrodes. In addition, the receptor reacts to a measured object to lead current variation which is transmitted by the plurality of electrodes.

19 Claims, 9 Drawing Sheets

BIOSENSOR, BIOSENSOR PACKAGE STRUCTURE HAVING SAME, AND METHOD FOR FABRICATING SAME

BACKGROUND

1. Technical Field

The present disclosure relates to a biosensor with electrodes comprising a plurality of carbon nanotubes, a biosensor package structure having the same, and a method for fabricating the same.

2. Description of Related Art

In general, a biosensor is a device that uses a specific biological element or a physical element similar to the biological element to get information from a measured object. The detected information is usually transduced by the biosensor into recognizable signals such as colors, fluorescence, or electrical signals. With technical advances in modem science, a biosensor is one of the devices that have developed rapidly.

A biosensor is composed of a receptor which reacts with a measured object to be detected, and electrodes which transmit current variation generated by the reaction between the receptor and the measured object. Examples of the receptor include an enzyme, antibody, antigen, membrane, receptor, cell, tissue, and deoxyribonucleic acid (DNA), which selectively reacts with the measured object. The electrodes are usually metal electrodes.

However, a width of each of the metal electrodes in the above-described biosensor is in a range from several micrometers (um) to dozens of micrometers. Thus, an amount of electrodes in a unit area of the biosensor is too few to influence accuracy and sensitivity of the same. Furthermore, the metal electrodes with poor inoxidability will shorten a lifetime of the biosensor.

Thus, there remains a need for providing a new biosensor which has greater accuracy, sensitivity, and a longer lifetime.

BRIEF DESCRIPTION OF THE DRAWINGS

Many aspects of the disclosure can be better understood with reference to the drawings. The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
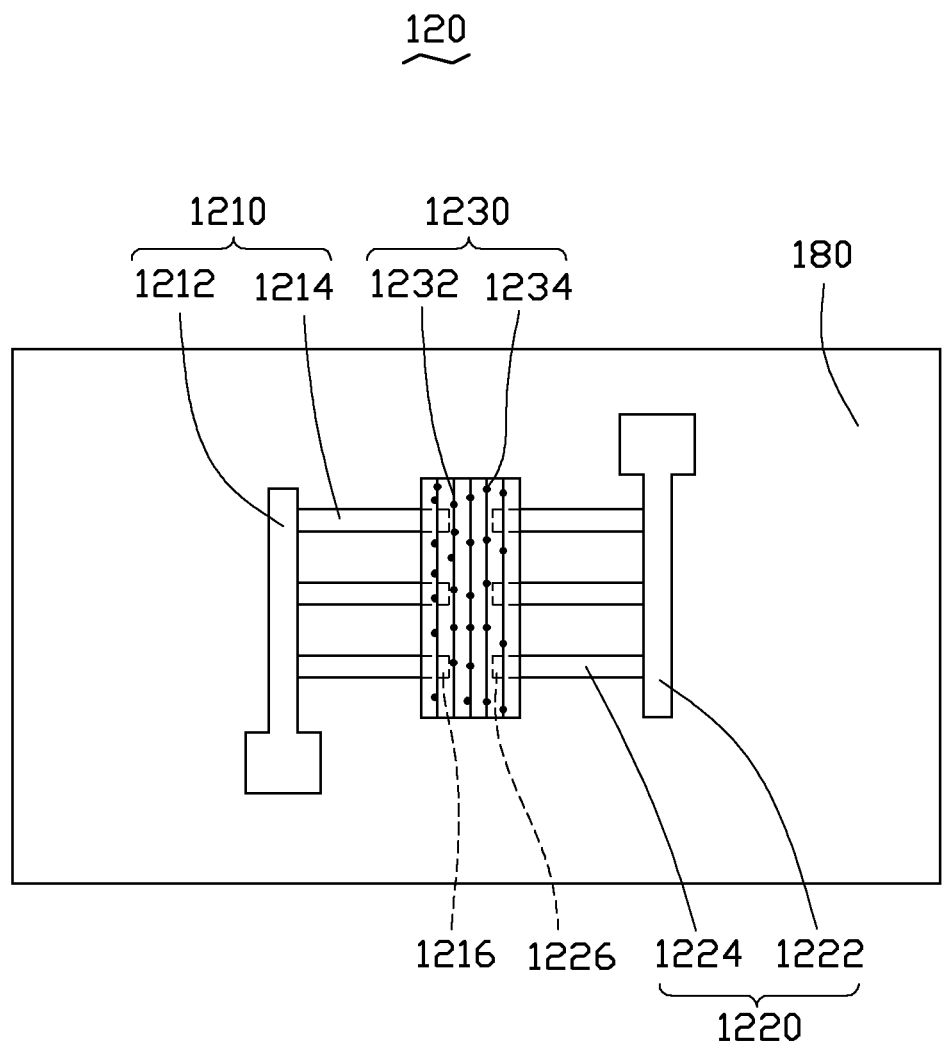
FIGS. 1, 2, and 3 are schematic views of embodiments of a biosensor.

According to one embodiment, a biosensor 120 as illustrated in FIG. 1 comprises a base 180 with a surface, two electrodes 1210 and 1220, and a receptor 1230. The two electrodes 1210 and 1220 are illustrated as a first electrode 1210 and a second electrode 1220 for exemplification and should not be treated as a limitation. The first electrode 1210, the second electrode 1220, and the receptor 1230 are located on the surface of the base 180 with an interval.

The first electrode 1210 comprises a first lead 1212 and a plurality of first carbon nanotubes 1214. The first carbon nanotubes 1214 are substantially parallel to each other, and comprise a first probe 1216. The first lead 1212 is electrically connected to one side of each of the first carbon nanotubes 1214 and an external circuit (not shown).

Similarly, the second electrode 1220 comprises a second lead 1222 and a plurality of second carbon nanotubes 1224. The second carbon nanotubes 1224 are substantially parallel to each other, and comprise a second probe 1226. The second lead 1222 is electrically connected to one side of each of the second carbon nanotubes 1224 and an external circuit (not shown).

The first carbon nanotubes 1214 and the second carbon nanotubes 1224 can be single-walled carbon nanotubes, double-walled carbon nanotubes, multi-walled carbon nanotubes, or combinations thereof. The diameter of the single-walled carbon nanotubes can be in the range from about 0.5 nanometers (nm) to about 50 nm. The diameter of the double-walled carbon nanotubes can be in the range from about 1 nm to about 50 nm. The diameter of the multi-walled carbon nanotubes can be in the range from about 1.5 nm to about 50 nm. In one embodiment, the length of the first carbon nanotubes 1214 and the second carbon nanotubes 1224 can be in a range from about 10 micrometers (um) to about 50 um.

More specifically, the first carbon nanotubes 1214 respectively correspond to the second carbon nanotubes 1224. Thus, the first probe 1216 of each of the first carbon nanotubes 1214 corresponds to the second probe 1226 of each of the second carbon nanotubes 1224. A distance between each two first carbon nanotubes 1214 is in a range from about 5 um to about 10 um. Similarly, a distance between each two second carbon nanotubes 1224 is in a range from about 5 um to about 10 um. A distance between the first probe 1216 of each of the first carbon nanotubes 1214 and the second probe 1226 of each of the second carbon nanotubes 1224 is equal to or less than 10 um. Furthermore, as shown in FIG. 1, an extended direction of each of the first carbon nanotubes 1214 is substantially parallel to an extended direction of each of the second carbon nanotubes 1224.

The first lead 1212 and the second lead 1222 can be conductive thick liquid, metal, carbon nanotubes, indium tin oxide (ITO), or any combination thereof. In one embodiment, the first lead 1212 and the second lead 1222 are made by printing or plating the conductive thick liquid. The conductive thick liquid comprises powdered metal, powdered glass with a low fusion point, and binder. The powdered metal is powdered silver. The binder is terpineol or ethyl cellulose. A weight percentage of the powdered metal is in a range from about 50% to about 90%. A weight percentage of the powdered glass with a low fusion point is in a range from about 2% to about 10%. A weight percentage of the binder is in a range from about 8% to about 40%.

The receptor 1230 comprises a plurality of carriers 1232 and a plurality of sensing materials 1234. The sensing materials 1234 are embedded in each of the carriers 1232. The first probe 1216 of each of the first carbon nanotubes 1214 and the second probe 1226 of each of the second carbon nanotubes 1224 are covered by the receptor 1230, such that the first electrode 1210 and the second electrode 1220 are electrically connected to each other. More specifically, the carriers 1232 define a plurality of conductive circuits, between the first carbon nanotubes 1214 of the first electrode 1210 and the second carbon nanotubes 1224 of the second electrode 1220, to electrically connect the sensing materials 1234.

The carriers 1232 can be carbon nanotubes, carbon fibers, amorphous carbon, graphite, or any combination thereof. In one embodiment, the carriers 1232 are carbon nanotubes with a plurality of functional groups. The functional groups can be carboxyl (—COOH) groups, hydroxyl (—OH) groups, aldehyde (—CHO) groups, amino (—NH2) groups, or any combination thereof.

In testing, the sensing materials 1234 embedded in the carriers 1232 react to a measured object such that current of the biosensor 120 is varied. The current variation of the biosensor 120 is transmitted by the first carbon nanotubes 1214 and the first lead 1212. Alternatively, the current variation of the biosensor 120 is transmitted by the second carbon nanotubes 1224 and the second lead 1222. The sensing materials 1234 can be antibodies, antigens, DNA, or any combination thereof. In one embodiment, the sensing materials 1234 are antibodies.

Figure 2:
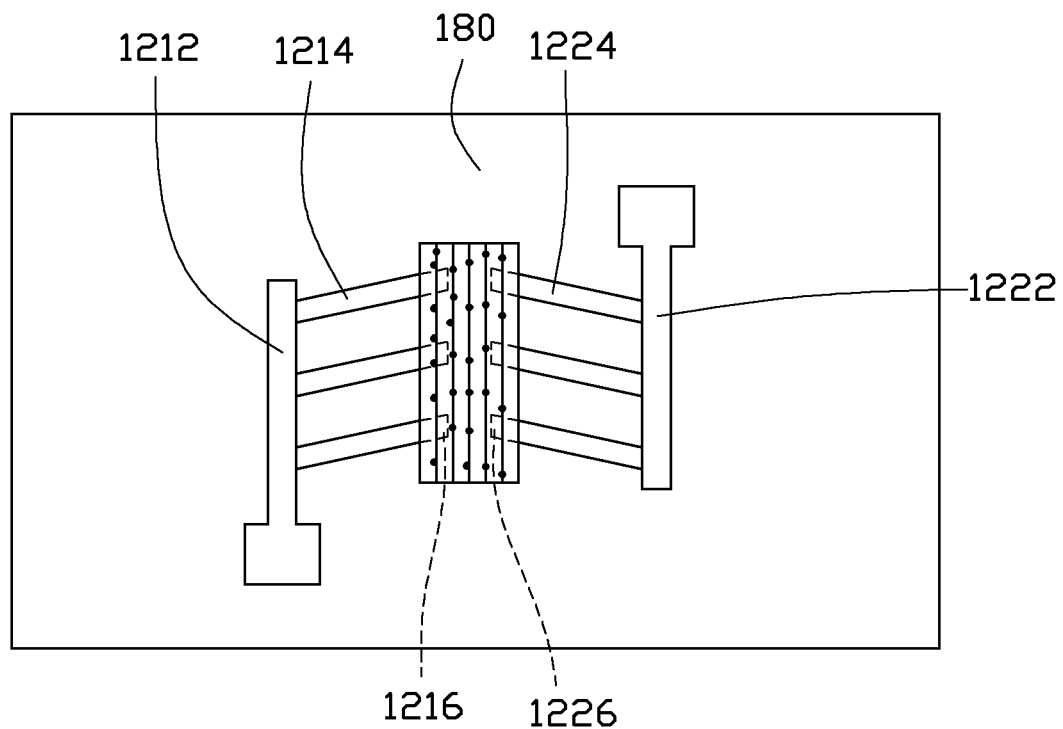

According to another embodiment, a biosensor 120 as illustrated in FIG. 2 comprises a base 180 with a surface, a first lead 1212, a plurality of first carbon nanotubes 1214, a second lead 1222, and a plurality of second carbon nanotubes 1224. Each of the first carbon nanotubes 1214 comprises a first probe 1216, and each of the second carbon nanotubes 1224 comprises a second probe 1226. Furthermore, as shown in FIG. 2, the first carbon nanotubes 1214 substantially parallel to each other and the second carbon nanotubes 1224 substantially parallel to each other form a specific angle.

Figure 3:
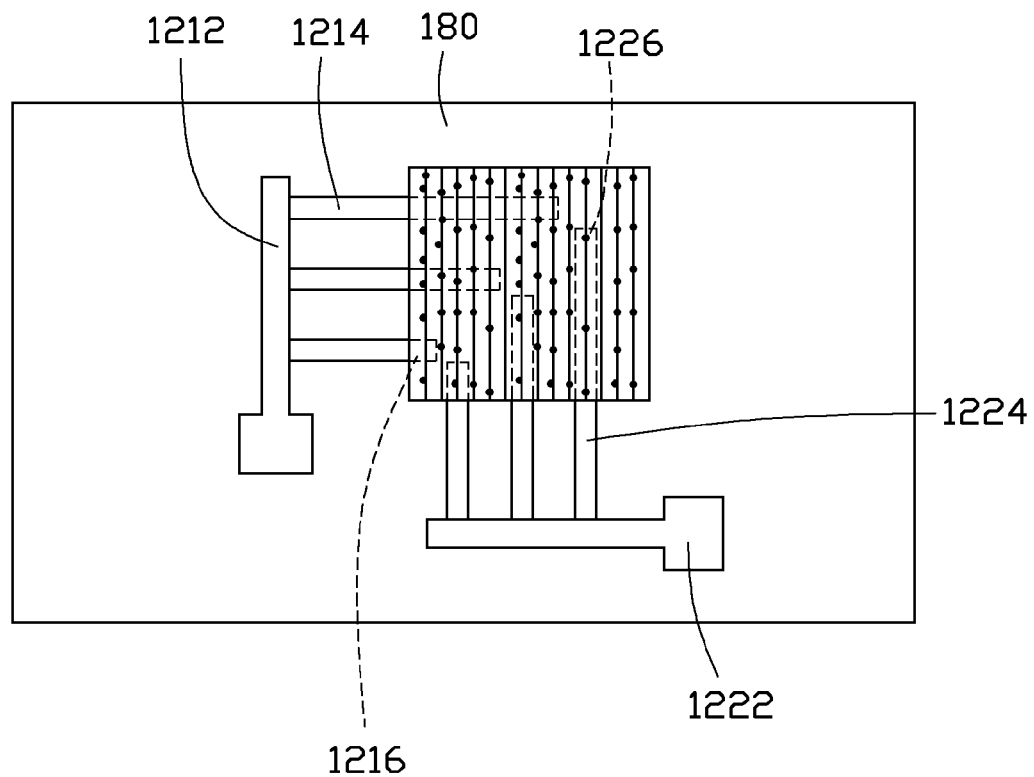

According to still another embodiment, a biosensor 120 as illustrated in FIG. 3 comprises a base 180 with a surface, a first lead 1212, a plurality of first carbon nanotubes 1214, a second lead 1222, and a plurality of second carbon nanotubes 1224. Each of the first carbon nanotubes 1214 comprises a first probe 1216, and each of the second carbon nanotubes 1224 comprises a second probe 1226. Furthermore, as shown in FIG. 3, an extended direction of each of the first carbon nanotubes 1214 is substantially perpendicular to an extended direction of each of the second carbon nanotubes 1224.

Figure 4:
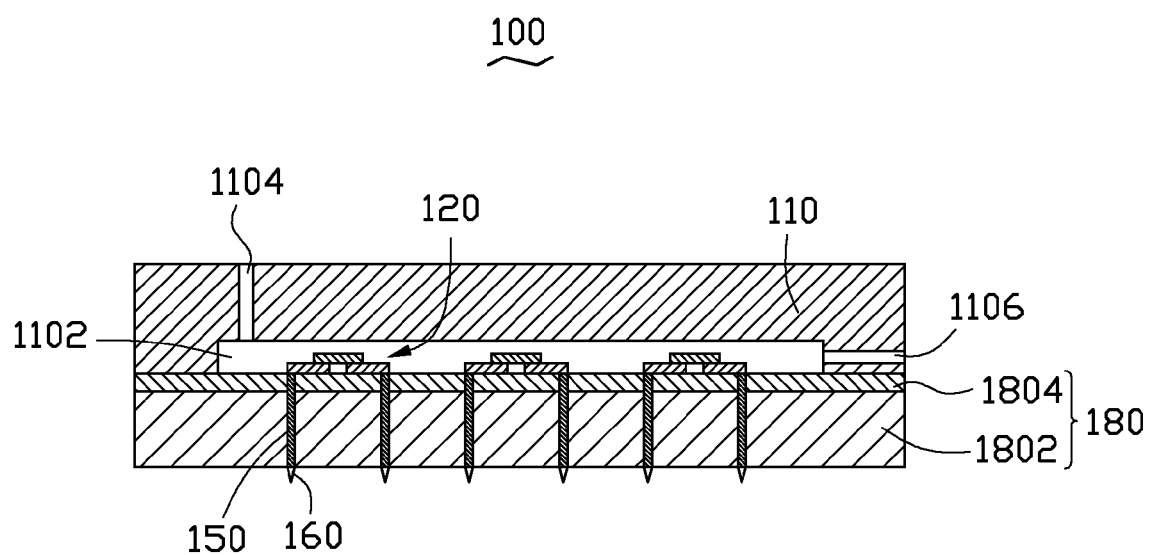
FIG. 4 is a schematic view of an embodiment of a biosensor package structure.

According to an embodiment, a biosensor package structure 100 as illustrated in FIG. 4 comprises a base 180 with a surface, a cover box 110, and a plurality of biosensors 120. The base 180 and the cover box 110 are plastered to each other to define a cavity 1102.

The base 180 which comprises conductive wires 150 can be a hard base or a flexible base. The hard base can be a ceramic base, a glass base, a quartziferous base, a siliceous base, an oxidative siliceous base, a diamond base, an alumina base, or any combination thereof. The flexible base can be a macromolecule base made by polydimethylsiloxane (PDMS), polycarbonate (PC), polymethyl methacrylate (PMMA), polyethylene (PE), polyimide (PI), polyethylene terephthalate (PET), polyether sulphone (PES), cellulose resin, polyvinylchloride (PVC), benzocyclobutene (BCB), acrylic resin, or any combination thereof. The base 180 comprises a siliceous slice 1802 with a surface and a silica layer 1804 formed on the surface of the siliceous slice 1802. In one embodiment, a thickness of the siliceous slice 1802 is in a range from about 0.5 millimeter (mm) to about 2 mm, and a thickness of the silica layer 1804 is in a range from about 100 um to about 500 um.

The cover box 110 comprises an input passage 1104 and an output passage 1106. The input passage 1104 is disposed in one side of the cover box 110, and the output passage 1106 is disposed in an opposite side of the same. In the embodiment, the cover box 110 is a poly dimethyl siloxane (PDMS) box. Diameters of the input passage 1104 and the output passage 1106 is in a range from about 200 um to about 400 um. The cavity 1102 is defined as a cuboid, a length of the cavity 1102 is in a range from about 5 mm to about 10 mm, a width of the same is in a range from about 0.2 mm to about 1 mm, and a height of the same is in a range from about 50 um to about 100 um.

The biosensors 120 are located on the surface of the base 180 side by side. The first electrode 1210 and the second electrode 1220 of each of the biosensors 120 are connected to pins 160 by the conductive wires 150. Thus, the biosensors 120 are electrically connected to the external circuit via the pins 160.

Accordingly, when the measured object is delivered to the cavity 1102 by the input passage 1104, and withdrawn from the cavity 1102 by the output passage 1106, the measured object will pass through the biosensors 120. Thus, the biosensors 120 react to the measured object such that current of each of the biosensors 120 is varied. Afterward, the current variation of each of the biosensors 120 is transmitted to the external circuit by the conductive wires 150 and the pins 160. Finally, the external circuit can get information from the measured object.

According to an embodiment, a method for fabricating a plurality of biosensors is illustrated in following steps. For exemplary purpose, the embodiment is adapted for fabricating the biosensors 120 of FIG. 1.

Figure 5:
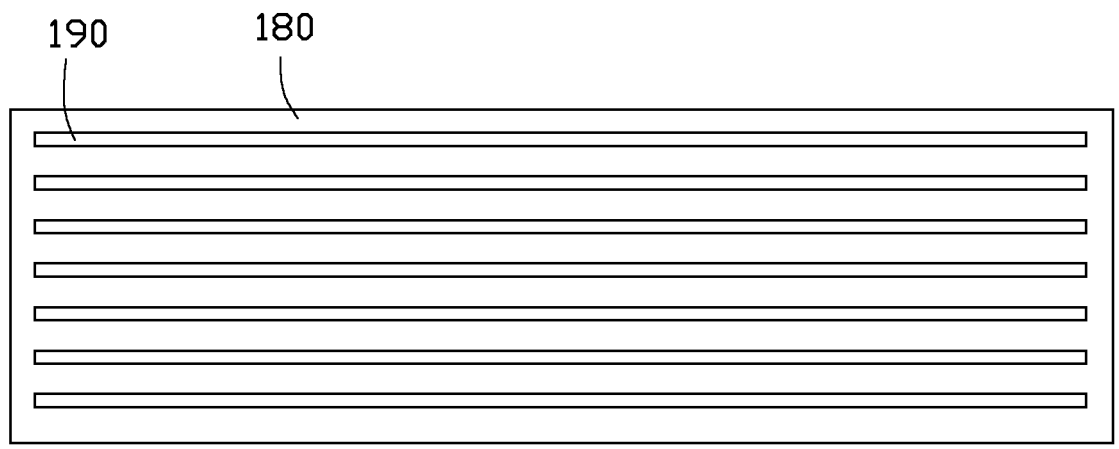
FIGS. 5, 6, 7, 8, and 9 show different schematic views of processes to manufacture a plurality of biosensors.

Referring to FIG. 5, in step one, a base 180 with a surface is provided, and a carbon nanotube array 190 is formed on the surface of the base 180. The carbon nanotube array 190 comprises a plurality of carbon nanotubes substantially parallel to each other.

Figure 6:
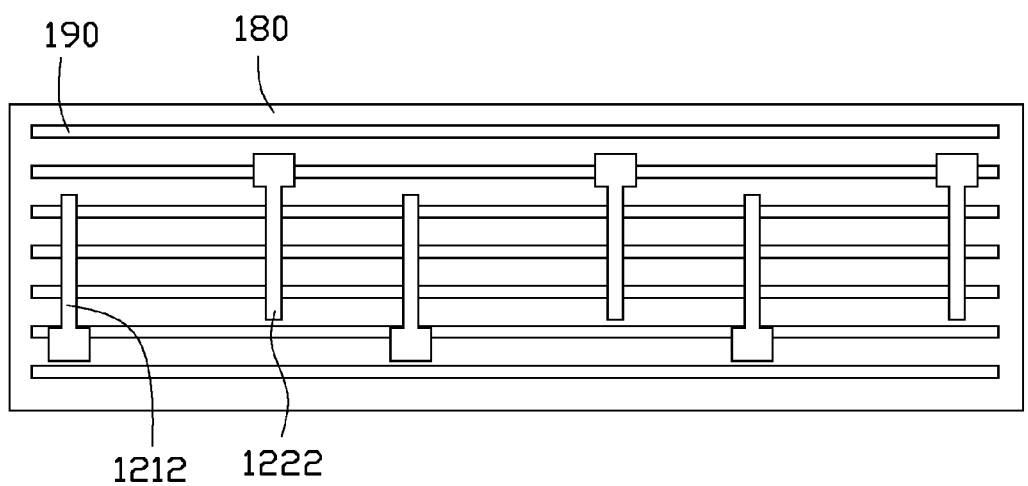

Referring to FIG. 6, in step two, a plurality of first leads 1212 and a plurality of second leads 1222 are formed by printing or plating conductive thick liquid on the surface of the base 180. Each of the first leads 1212 corresponds to each of the second leads 1222, and are electrically connected to each other by at least one of the carbon nanotubes of the carbon nanotube array 190.

Figure 7:
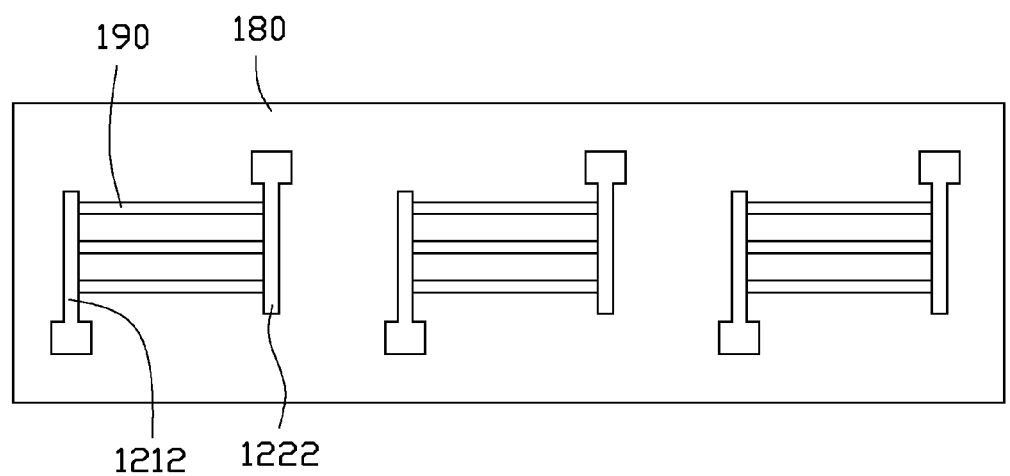

Referring to FIG. 7, in step three, a part of the carbon nanotubes of the carbon nanotube array 190 is eliminated. Thus, the carbon nanotubes between each of the first leads 1212 and each of the second leads 1222 remain on the surface of the base 180.

Figure 8:
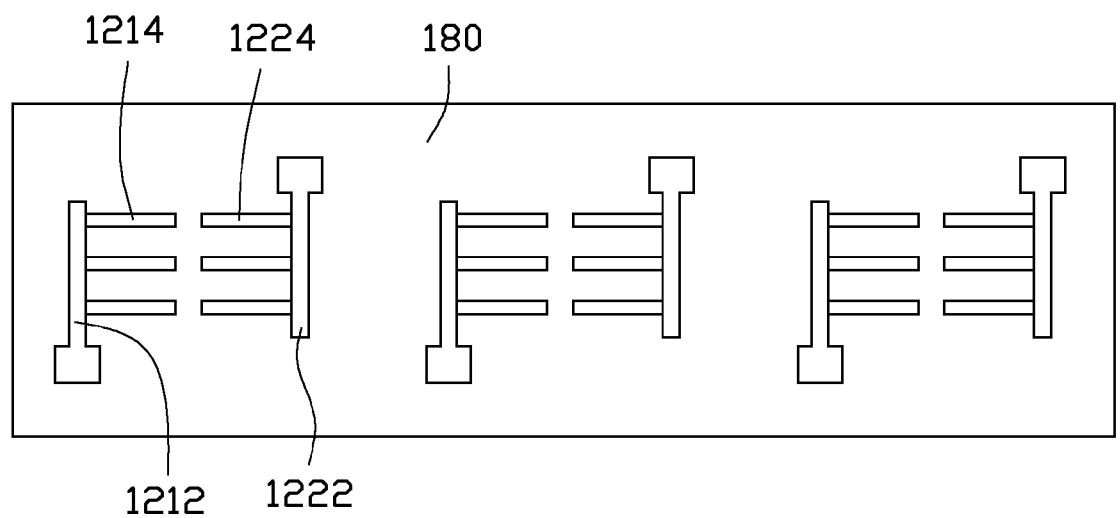

Referring to FIG. 8, in step four, the carbon nanotubes between each of the first leads 1212 and each of the second leads 1222 are cut to form a plurality of first carbon nanotubes 1214 and a plurality of second carbon nanotubes 1224. Each of the first carbon nanotubes 1214 corresponds to each of the second carbon nanotubes 1224.

Figure 9:
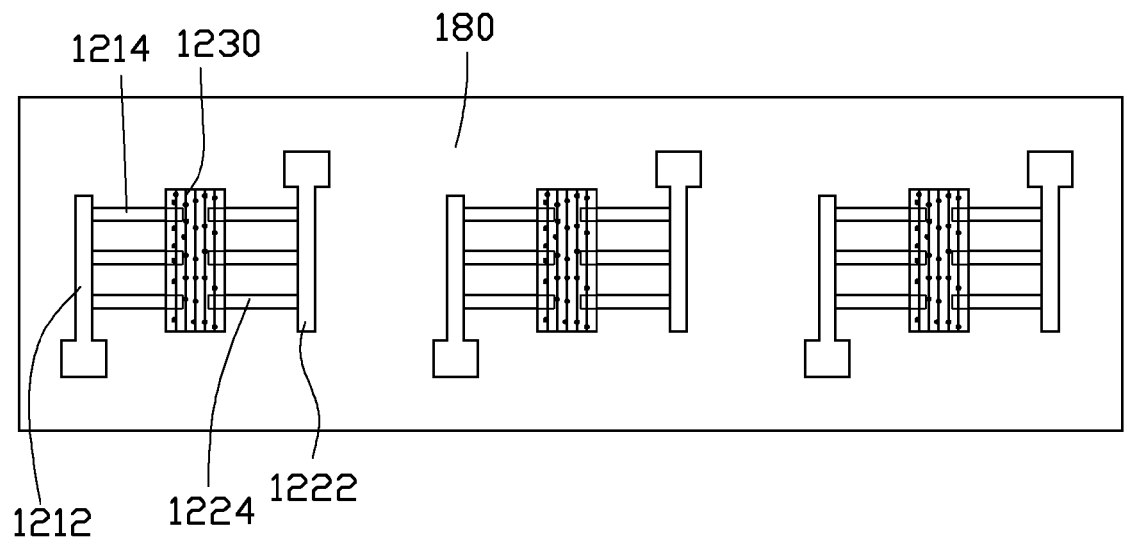

Referring to FIG. 9, in step five, receptors 1230 are fabricated between each of the first leads 1212 and each of the second leads 1222. Thus, the first carbon nanotubes 1214 and the second carbon nanotubes 1224 between each of the first leads 1212 and each of the second leads 1222 are electrically connected to each other by one of the receptors 1230.

Accordingly, the present disclosure is capable of transmitting current variation of a biosensor via electrodes with carbon nanotubes. In addition, a width each of the electrodes can be decreased without influencing the accuracy and sensitivity of the biosensor. Thus, the biosensor can be easily manufactured with greater accuracy, sensitivity, and a longer lifetime.

It is to be understood that the above-described embodiments are intended to illustrate rather than limit the disclosure. Any elements described in accordance with any embodiments is understood that they can be used in addition or substituted in other embodiments. Embodiments can also be used together. Variations may be made to the embodiments without departing from the spirit of the disclosure. The above-described embodiments illustrate the scope of the disclosure but do not restrict the scope of the disclosure.

What is claimed is:

1. A biosensor, comprising:
a plurality of electrodes comprising a first electrode and a second electrode, wherein the first electrode comprises a plurality of first carbon nanotubes substantially parallel to each other, the second electrode comprises a plurality of second carbon nanotubes substantially parallel to each other; and
a receptor located between the plurality of electrodes and electrically connected to the plurality of first carbon nanotubes and the plurality of second carbon nanotubes, the receptor reacting to a measured object to vary current of the biosensor,
wherein the current variation of the biosensor is transmitted by the plurality of electrodes.

2. The biosensor as claimed in claim 1, wherein the biosensor further comprises a base with a surface, and the plurality of electrodes are located on the surface of the base with an interval.

3. The biosensor as claimed in claim 1, wherein the plurality of first carbon nanotubes respectively correspond to the plurality of second carbon nanotubes.

4. The biosensor as claimed in claim 1, wherein the first electrode further comprises a first lead electrically connected to the plurality of first carbon nanotubes, and a second lead electrically connected to the plurality of second carbon nanotubes.

5. The biosensor as claimed in claim 1, wherein an extended direction of each of the plurality of first carbon nanotubes is substantially parallel to an extended direction of each of the plurality of second carbon nanotubes.

6. The biosensor as claimed in claim 1, wherein an extended direction of each of the plurality of first carbon nanotubes is substantially perpendicular to an extended direction of each of the plurality of second carbon nanotubes.

7. The biosensor as claimed in claim 1, wherein a distance between every two first carbon nanotubes of the plurality of first carbon nanotubes is in a range from about 5 micrometers (um) to about 10 um, and a distance between every two second carbon nanotubes of the plurality of second carbon nanotubes is in a range from about 5 um to about 10 um.

8. The biosensor as claimed in claim 1, wherein each of the plurality of first carbon nanotubes comprises a first probe, each of the plurality of second carbon nanotubes comprises a second probe, the first probe of each of the plurality of first carbon nanotubes corresponds to the second probe of each of the plurality of second carbon nanotubes.

9. The biosensor as claimed in claim 8, wherein a distance between the first probe of each of the plurality of first carbon nanotubes and the second probe of each of the plurality of second carbon nanotubes is equal to or less than 10 micrometers (um).

10. The biosensor as claimed in claim 1, wherein the receptor comprises at least one carrier and sensing material embedded in the at least one carrier.

11. The biosensor as claimed in claim 10, wherein the at least one carrier is selected from the group consisting of a carbon nanotube, a carbon fiber, amorphous carbon, graphite, and any combination thereof.

12. The biosensor as claimed in claim 10, wherein the sensing material is selected from the group consisting of antibodies, antigens, deoxyribonucleic acid (DNA), and any combination thereof.

13. The biosensor as claimed in claim 10, wherein the at least one carrier defines a conductive circuit between the plurality of carbon nanotubes of the plurality of electrodes.

14. A biosensor package structure for a biosensor comprising a plurality of electrodes comprising a first electrode and a second electrode, wherein the first electrode comprises a plurality of first carbon nanotubes substantially parallel to each other, the second electrode comprises a plurality of second carbon nanotubes substantially parallel to each other, the biosensor package structure further comprises a receptor located between the plurality of electrodes and electrically connected to the plurality of first carbon nanotubes and the plurality of second carbon nanotubes, the receptor reacting to a measured object to vary current of the biosensor transmitted by the plurality of electrodes, the package comprising:
a base;
a cover box for defining a cavity with the base;
a plurality of passages in contact with the cavity,
wherein the measured object passes through the cavity via the plurality of passages, and the biosensor is located in the cavity and reacts to the measured object to vary current of the biosensor.

15. The biosensor package structure as claimed in claim 14, wherein the plurality of passages comprises an input passage and an output passage, the measured object is delivered to the cavity by the input passage, and withdrawn from the cavity by the output passage.

16. A biosensor, comprising:
a first electrode comprising a plurality of first carbon nanotubes each having a first end and a second end;
a second electrode comprising a plurality of second carbon nanotubes each having a third end and a fourth end, wherein the first end of each of the first carbon nanotubes corresponds to the fourth end of each of the second carbon nanotubes in a one to one manner and there is a distance between the first end and the fourth end, distances between first ends and fourth ends form a continuous channel, each of distances between first ends and fourth ends is equal; and
a receptor located in the channel between the first carbon nanotubes and the second carbon nanotubes.

17. The biosensor as claimed in claim 16, wherein the plurality of first carbon nanotubes is substantially parallel to each other, the plurality of second carbon nanotubes is substantially parallel to each other.

18. The biosensor as claimed in claim 16, wherein the each of the distances between the first ends and the fourth ends is equal to or less than 10 micrometers (um).

19. The biosensor as claimed in claim 16, wherein an extended direction of each of the plurality of first carbon nanotubes is substantially parallel to an extended direction of each of the plurality of second carbon nanotubes.

* * * * *